United States Patent [19]

Takayama

[11] 4,291,961
[45] Sep. 29, 1981

[54] APPARATUS FOR ENDOSCOPIC PHOTOGRAPHY

[75] Inventor: Syuichi Takayama, Hachioji, Japan

[73] Assignee: Olympus Optical Company, Ltd., Japan

[21] Appl. No.: 133,668

[22] Filed: Mar. 25, 1980

[30] Foreign Application Priority Data

Apr. 16, 1979 [JP] Japan ................... 54-46975

[51] Int. Cl.³ ............................ A61B 1/04; A61B 3/14
[52] U.S. Cl. ................................................... 354/62
[58] Field of Search ...................... 354/62, 132, 141; 128/6

[56] References Cited

U.S. PATENT DOCUMENTS 3,599,630 8/1971 Sato et al. ........................ 354/62 X
4,086,583 4/1978 Takahashi ........................... 354/62

Primary Examiner—Michael L. Gellner
Attorney, Agent, or Firm—Ostrolenk, Faber, Gerb & Soffen

[57] ABSTRACT

An apparatus for endoscopic photography enables a picture to be taken of the interior of a coeliac cavity by coupling a camera and a light source unit with an endoscope. The apparatus comprises at least four delay circuits to achieve automatic control of a series of operations which are required to take a picture so that a proper exposure to a film surface is given.

9 Claims, 9 Drawing Figures

APPARATUS FOR ENDOSCOPIC PHOTOGRAPHY

BACKGROUND OF THE INVENTION

The invention relates to an apparatus for endoscopic photography, and more particularly, to such apparatus in which an automatic exposure mechanism disposed within a light source unit that is in turn connected to an endoscope is controlled in response to a signal from a photometric circuit disposed within a photographic camera which is mounted on the endoscope.

With a conventional apparatus for endoscopic photography, a light source which emits light for the purpose of taking a picture is activated in synchronism with the closure of X- or FP-contacts which represent electrical contacts disposed within a camera for the purpose of synchronization.

However, with an apparatus for endoscopic photography of the type utilizing a light source unit in which a switching operation is made in response to a shutter release operation of the camera between a diagnostic light source used for illumination purpose and another photographing light source used for taking a picture, the use of X-contacts presents a difficulty in that since they are closed simultaneously with the opening of the shutter, a film surface is exposed to diagnostic illumination light which continues to be emitted during the switching time, thereby preventing an accurate control of the exposure. In addition, since the photometry for the purpose of an automatic exposure control is initiated concurrently with the closure of X-contacts, it is difficult to derive a precise estimation of a contribution to the exposure which results from the diagnostic illuminating light during the switching time. Consequently, the amount of the diagnostic illuminating light which is maintained during the switching time associated with the light source causes an error in the exposure.

Where FP-contacts are used, it is necessary to effect a switching operation from a light source associated with the diagnostic illumination to another light source used for taking a picture in timed relationship with the closure of a synchro-contact, which is closed 11±3 msec before the shutter begins to be opened. However, the required switching control is very difficult to achieve, and a wrong timing in the switching operation disadvantageously causes an error in the exposure.

SUMMARY OF THE INVENTION

It is an object of the invention to eliminate described disadvantages of the prior art, by providing an apparatus for endoscopic photography which includes at least four, and preferably five, delay circuits, which serve the following purposes. A first delay circuit is for causing a shutter to be opened at a time after a diagnostic illuminating light has ceased to be incident before taking a picture. A second delay circuit initiates the operation of an exposure calculation circuit subsequent to the opening of the shutter. A third delay circuit is for allowing the incidence of light from an object being photographed subsequent to the initiation of operation of the exposure calculation circuit. A fourth delay circuit is for switching a light source on to produce diagnostic illuminating light upon completion of the closure of the shutter, and a fifth delay circuit allows an automatic film winding operation (optionally) upon completion of the closure of the shutter. These delay circuits allow accurate control of the exposure of a film surface.

In an apparatus for endoscopic photography in which an automatic exposure mechanism disposed in a light source unit which is connected to an endoscope is controlled in accordance with a signal from a photometric circuit provided for the purpose of automatic exposure control within a photographic camera which is mounted on the endoscope, the invention provides; a first delay circuit for causing a shutter to begin to be opened after diagnostic illuminating light ceases to be incident into the camera in response to the depression of a shutter button associated with the camera; a second delay circuit for initiating the operation of an exposure calculaton circuit after the opening of the shutter; a third delay circuit for allowing the entry of light from an object being photographed into the camera after the initiation of operation of the exposure calculation circuit; a fourth delay circuit for switching a light source to produce diagnostic illuminating light after an exposure of film disposed within the camera is terminated and the closure of the shutter is completed; and a fifth delay circuit for initiating an automatic film winding operation, optionally, upon completion of the closure of the shutter.

No light from an external source other than light from an object being photographed is allowed to impinge into the interior of the camera during the time the shutter remains open, and the exposure calculation circuit responds to the light from the object by effecting a calculation of the amount of exposure in order to control a photographing light source. In this manner, an automatic exposure control of a high precision is achieved.

DESCRIPTION OF PREFERRED EMBODIMENTS

Figure 1:
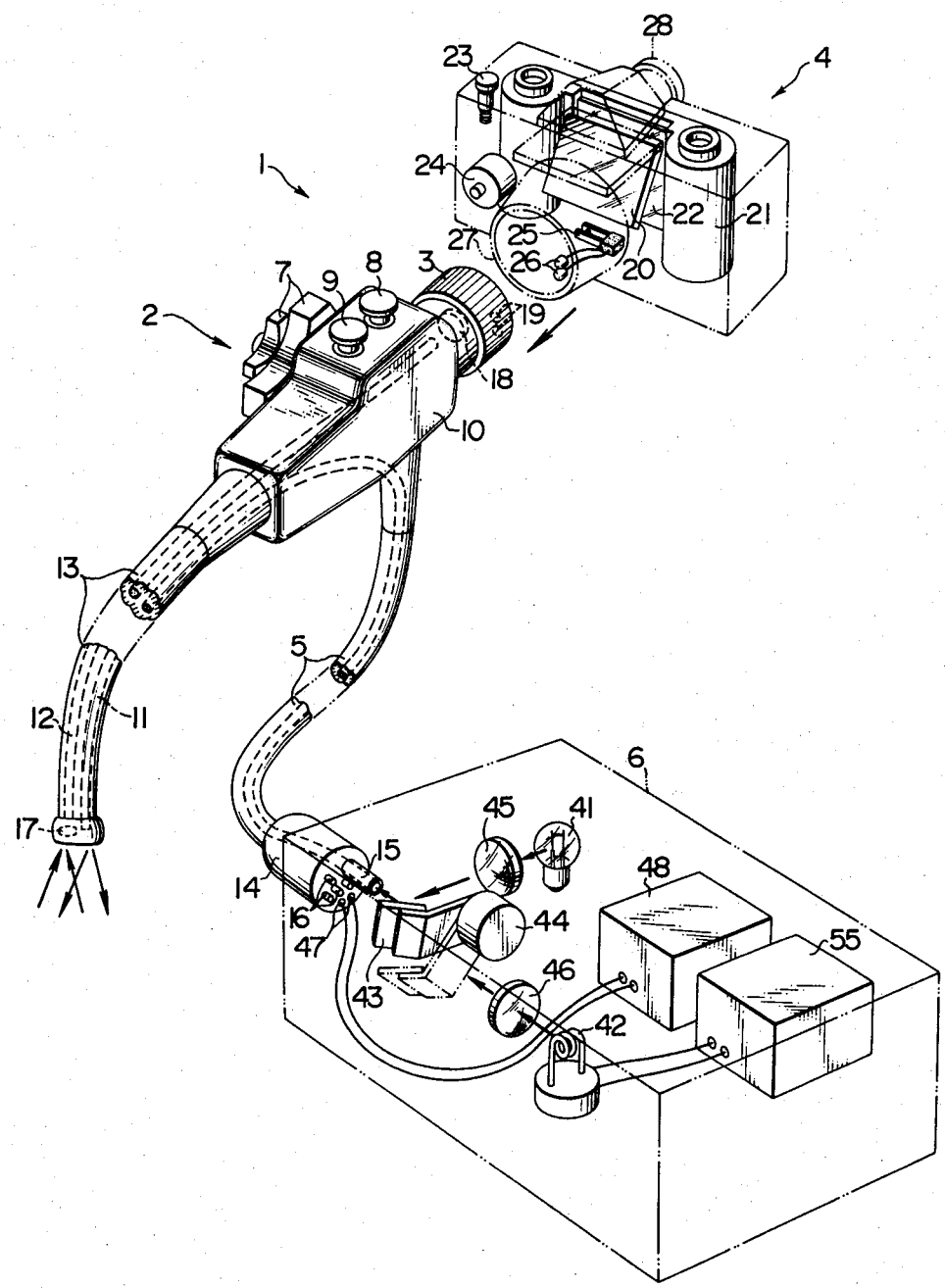
FIG. 1 is a perspective view of the essential parts of an apparatus for endoscopic photography according to one embodiment of the invention.

Referring to FIG. 1, there is shown an apparatus for endoscopic photography according to one embodiment of the invention in schematic form. In this Figure, an apparatus 1 for endoscopic photography comprises a combination of an endoscope 2 which is well known in itself, a photographic camera 4 which is adapted to be mounted on the eyepiece assembly 3 of the endoscope 2, and a light source unit 6 which is connected to the endoscope 2 through a light guide tube 5.

The endoscope 2 comprises a proximate end operator 10 which is provided with a knob 7 which is operated to effect a bending operation, an air/water supply button 8 and a suction button 9, the proximate operator enabling a variety of operations to be performed by the endoscope, at a point external of the endoscope. In addition, the endoscope comprises a portion 13 which is adapted to be inserted into a coeliac cavity and formed by a flexible tube connected to the front end of the proximate end operator 10 and internally housing bundles of optical fibers 11, 12 which define a light guide and an image guide, respectively. The light guide is also passed through the light guide tube 5. The eyepiece assembly 3 is located on the rear end of the proximate operator 10. The other end of the light guide tube 5 is provided with a light source connector 14 for connection of the endoscope 2 with the light source unit 6. A light guide connector 15 and a plurality of electrical terminals 16 project out of the end face of the connector 14. An objective lens 17 is disposed in the distal end of the endoscope of the endoscope portion 13 in alignment with one of the end faces of the image guide 12. An eyepiece 18 is disposed in the eyepiece assembly 3 in alignment with the other end face of the image guide 12. When the camera 4 is mounted on the eyepiece assembly 3, the eyepiece 18 also serves as part of the lens of the camera 4. A plurality of electrical terminals 19 are disposed in the outer end face of the eyepiece assembly 3, and correspond to the individual terminals 16 disposed on the connector 14.

The camera 4 shown is a single lens reflux camera having a mirror shutter 20, and is adapted to have a film cassette 21 loaded therein. The cassette contains a length of photographic film 22, one exposed frame of which is wound up by a winding motor 24 after an exposure step in a manner controlled by the electrical circuit to be described later. The camera also includes a synchro contact 25 connected to electrical terminals 26 which are disposed so as to be aligned with terminals 19 on the endoscope 2. The electrical terminals 26 are adapted to be closed in response to the depression of a shutter release button 23. The camera 4 includes a mating part 27 which projects from the front surface thereof and which can be fitted over the eyepiece assembly 3, whereby it is mounted on the endoscope 2. Before or after a picture is taken, a viewfinder 28 of the camera may be viewed to observe the interior of the coeliac cavity.

Figure 2:
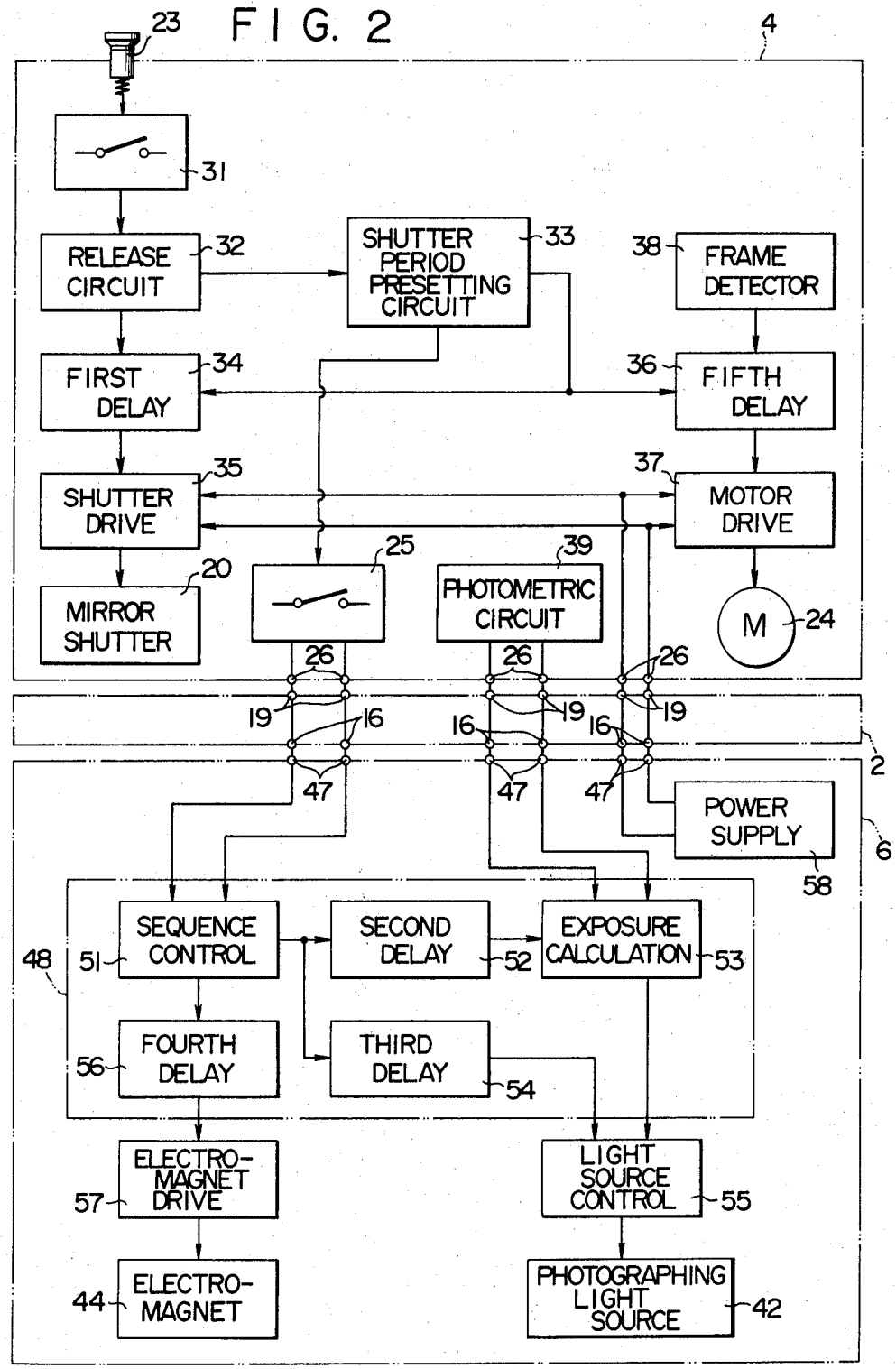
FIG. 2 is a block diagram of an electrical circuit contained in the apparatus shown in FIG. 1.

FIG. 2 shows an electrical circuit which is housed within the camera 4. Specifically, it comprises a shutter release switch 31 which is closed in response to the depression of the shutter release button 23, a release circuit 32 which starts to operate upon closure of the switch 31. An exposure period presetting circuit 33 initiates a fixed shutter period in response to an output from the release circuit 32. A first delay circuit 34 becomes operative after a light path switching electromagnet 44 (see FIG. 1) of the light source unit 6 has been operated by an output from the release circuit 32 to change the light path. A shutter drive circuit 35 responds to a delayed output from the first delay circuit 34 to drive the mirror shutter 20 to move upward. A fifth delay circuit 36 becomes operative upon completion of a downward movement of the mirror shutter 20 in response to an output produced by the circuit 33 after the fixed shutter period. A motor drive circuit 37 responsive to a delayed output from the fifth delay circuit 36 operates the winding motor 24. A frame detector 38 operates to detect the winding of one exposed frame of the film 22 and acts through the delay circuit 36 and the motor drive circuit 37 to interrupt the operation of the motor 24, and a photometric circuit 39 is provided for the purpose of automatic exposure control and includes a photometric light receiving element. When the shutter period presetting circuit 33 begins to time the fixed shutter period, it produces an output which is applied to the synchro contact 25. The circuit 33 also produces an output at the termination of the fixed shutter period which is applied to the first delay circuit 34. It is to be noted that the shutter drive circuit 35, the motor drive circuit 37, the synchro contact 25 and the photometric circuit 39 are connected to electrical terminals 26 which correspond to the electrical terminals 19.

Returning to FIG. 1, the light source unit 6 comprises a light source 41 which is used to produce light for diagnostic illumination and another light source 42 which is utilized when taking a picture. A light path switching, reflecting mirror 43 introduces the light from either light source 41 or 42 into the light guide connector 15. A light path switching electromagnet 44 operates the reflecting mirror 43. A condencer lens 45 for diagnostic illuminating light is disposed in the light path between the light source 41 and the light guide connector 15. Another condencer lens 46 for photograph taking light is disposed in the light path between the light source 42 and the connector 15. An automatic exposure control circuit 48 connected to electrical terminals 47 is disposed in alignment with the connection terminals 16 and receives various electrical signals from the camera 4, and a photographing light source control circuit 55 controls the light emission from the light source 42.

FIG. 2 also shows an electrical circuit such as an automatic exposure control circuit 48 which is disposed within the light source unit 6. Specifically, it comprises a sequence control circuit 51 connected to the synchronizing contact 25 through the electrical terminals 47. A second delay circuit 52 receives an output from the sequence control circuit 51 and becomes operative after the mirror shutter 20 has been opened. An exposure calculation circuit 53 is responsive to an output from the second delay circuit for calculating the amount of exposure in accordance with a signal supplied from the automatic exposure photometric circuit 39 provided in the camera 4. A third delay circuit 54 receives an output from the sequence control circuit 51 and becomes operative after the exposure calculation circuit 53 has begun to operate. A photographing light source control circuit 55 receives an output from the third delay circuit 54 and operates to initiate the light emission from the photographing light source 42 in response to an output from the third delay circuit 54 and to terminate the light emission thereof in response to an output from the exposure calculation circuit 53. A fourth delay circuit 56 begins to produce an output signal in response to a close signal indicative of the closure of the synchronizing contact 25 and terminates the output signal upon completion of the closure of the mirror shutter 20. An electromagnet drive circuit 57 is provided and is responsive to an output from the fourth delay circuit 56 to energize the light path switching electromagnet 44, and a power supply unit 58 is connected to and feed the shutter drive circuit 35 and the motor drive circuit 37 of the camera 4 through the electrical terminals 47. While not shown, the light source 41 which is utilized to produce diagnostic illuminating light is fed from the power supply unit 58 and normally continues to produce light whenever a main switch (not shown) of the light source unit 6 is turned on.

The operation of the apparatus 1 will now be described with reference to the timing chart of FIG. 3.

Initially, the connector 14 of the endoscope 2 is connected to the light source unit 6 while the camera 4 is mounted on the eyepiece assembly 3. By viewing the viewfinder 28, an area of the coeliac cavity a picture of which is desired to be taken is brought into the field of sight. Thereupon, the shutter release button 23 may be depressed, as indicated by graph A of FIG. 3. The shutter release switch 31 is then closed to operate the release circuit 32, an output of which is fed to the shutter period presetting circuit 33 and the first delay circuit 34. In response to an output from the release circuit 32, the circuit 33 closes the synchronizing contact 25, as indicated by graph B of FIG. 3. In response to a close signal indicative of the closure of the synchronizing contact 25, the sequence control circuit 51 produces outputs which are individually applied to the second, the third and the fourth delay circuit 52, 54 and 56, respectively. In response thereto, the fourth delay circuit 56 immediately produces an output as shown by graph J, which is fed to the electromagnet drive circuit 57, energizing the light path switching electromagnet 44 as shown by graph C. In this manner, the reflecting mirror 43 is moved out of the diagnostic light path, preventing the light from the light source 41 from being led out of the light source unit 6 through the light guide connector 15, as indicated by graph M. As indicated by graph I, the photographing light source 42 is not yet activated, so that light input to the camera is interrupted temporarily.

Subsequently, in response to a close signal indicative of the closure of the shutter release switch 31 which is produced by the release circuit 32, the first delay circuit 34 produces an output which is fed to the shutter drive circuit 35 after a time interval $T_1$ when the electromagnet 44 is fully energized to prevent the incidence of the diagnostic light into the camera 4, as indicated by graph D. This output from the shutter drive circuit 35 operates, whereby the mirror shutter 20 is driven for upward motion, as indicated by graph E. However, at this point in time, there is neither diagnostic light which is incident on the camera 4, nor illumination from the photographing light source 42, so that the film surface remains unexposed.

Figure 3:
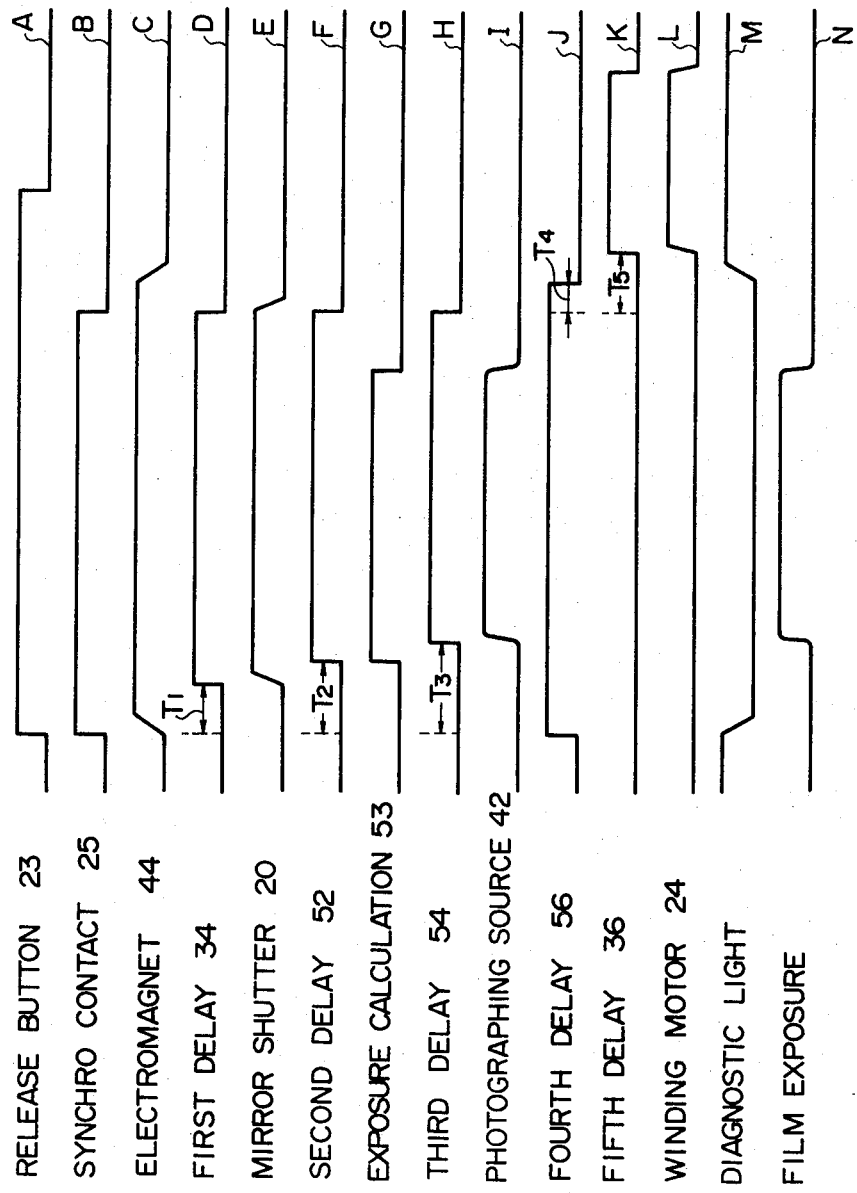
FIG. 3 is a timing chart illustrating the various timings of operation of the electrical circuit shown in FIG. 2.

Then, in response to the close signal associated with the synchronizing contact 25 which is produced by the sequence control circuit 51, the second delay circuit 52 produces an output which is fed to the exposure calculation circuit 53 after a time interval $T_2$ when the mirror shutter 20 becomes fully open, as indicated by graph F of FIG. 3. In response to this output, the exposure calculation circuit 53 begins integrating the amount of exposure imparted to the film surface, as indicated by graph G of FIG. 3. However, there is no incidence of light into the camera 4 at this time, and hence the automatic exposure, photometric circuit 39 produces no output, and the exposure calculation circuit 53 remains quiescent.

Subsequently, in response to the close signal associated with the synchronizing contact 25 which is fed from the sequence control circuit 51, the third delay circuit 54 produces an output which is fed to the photographing light source control circuit 55 after a time interval $T_3$, as indicated by graph H. It is to be noted that the exposure calculation circuit 53 begins its operation before the time interval $T_3$ passes. The control circuit 55 responds thereto by causing the photographing light source 42 to emit light, as indicated by graph I. Thereupon, the photographing light is fed through the light guide connector 15 and the light guide 11 to irradiate the interior of a coeliac cavity, and is reflected by the internal wall of the cavity to be transmitted through the image guide 12 to be incident into the camera 4, whereby it is focused onto the film surface, which is therefore exposed, as shown by graph N. Part of the light which is incident into the camera 4 in this manner is also supplied to the photometric circuit 39, which produces an electrical signal which is supplied to the exposure calculation circuit 53 which has been in its quiescent condition. Thus, the circuit 53 begins integrating the amount of exposure applied.

As the exposure of the film surface to the photographing light continues, the exposure calculation circuit 53 determines that a proper amount of light has been applied to the film surface for purpose of exposure, whereupon it ceases to produce an output fed to the control circuit 55, as indicated by graph G, thereby terminating the light emission from the photographing light source 42, as indicated by graph I. The film surface then ceases to be exposed, with an image of an object being photographed formed therein with a proper exposure.

After the given shutter period since the mirror shutter 20 has been opened in the manner mentioned above, the shutter period presetting circuit 33 is disabled, and a resulting disable signal is applied to the first delay circuit 34, the output of which is then terminated as indicated by graph D, whereby the shutter drive circuit 35 ceases to operate, allowing the mirror shutter 20 to move down as indicated by graph E. The disable signal from the presetting circuit 33 is also applied to the synchronizing contact 25 to open it, as indicated by graph B, and an open signal indicative of the opening of this contact is fed through the sequence control circuit 51 to the second, the third and the fourth delay circuit 52, 54, 56. In response to the open signal, the second and the third delay circuit 52, 54 cease to produce their output as indicated by graphs F and H, respectively, while the fourth delay circuit 56 ceases to produce its output after a time interval $T_4$ since the opening of the synchronizing contact 25 which is sufficient to allow the mirror shutter 20 to be completely closed, as indicated by graph J. The electromagnet drive circuit 57 is then rendered inoperative, whereby the electromagnet 44 is deenergized as indicated by graph C of FIG. 3, returning the reflecting mirror 43 to its normal position. Accordingly, the light from the diagnostic light source 41 is transmitted through the light guide connector 15 to irradiate the internal wall of the coeliac cavity, as indicated by graph M of FIG. 3, whereby it is reflected to be incident into the camera 4. However, since the mirror shutter 20 is closed at this time, the diagnostic light cannot cause an exposure of the film surface.

The disable signal from the shutter period presetting circuit 33 is also applied to the fifth delay circuit 36, which produces an output which is fed to the motor drive circuit 37 after a time interval $T_5$ since the opening of the synchronizing contact 25 which is sufficient to complete the closing operation of the mirror shutter 20, as indicated by graph K, thereby driving the motor 24 to wind up the film 22 as indicated by graph L of FIG. 3. The film winding operation is detected by the frame detector 38, which produces a signal at the completion of one exposed frame of the film 22 having been wound up, the signal being applied to the motor drive circuit 37 which ceases to produce its output in response thereto, thus terminating the energization of the motor 24.

In this manner, a series of operations required to take a single picture including the shut-off of the diagnostic light, opening of the mirror shutter 20, activation of the exposure calculation circuit 53, light emission from the photographing light source 42, an automatic illumination control by the exposure calculation circuit 53, closing of the mirror shutter 20, resumption of the diagnostic light, and a winding operation of an exposed film frame are sequentially controlled, providing an exposure of the film surface as indicated by graph N of FIG. 3. The amount of exposure imparted to the film surface is controlled to a high accuracy since only the photographing light is used and the exposure calculation circuit 53 determines a proper exposure.

Figure 4:
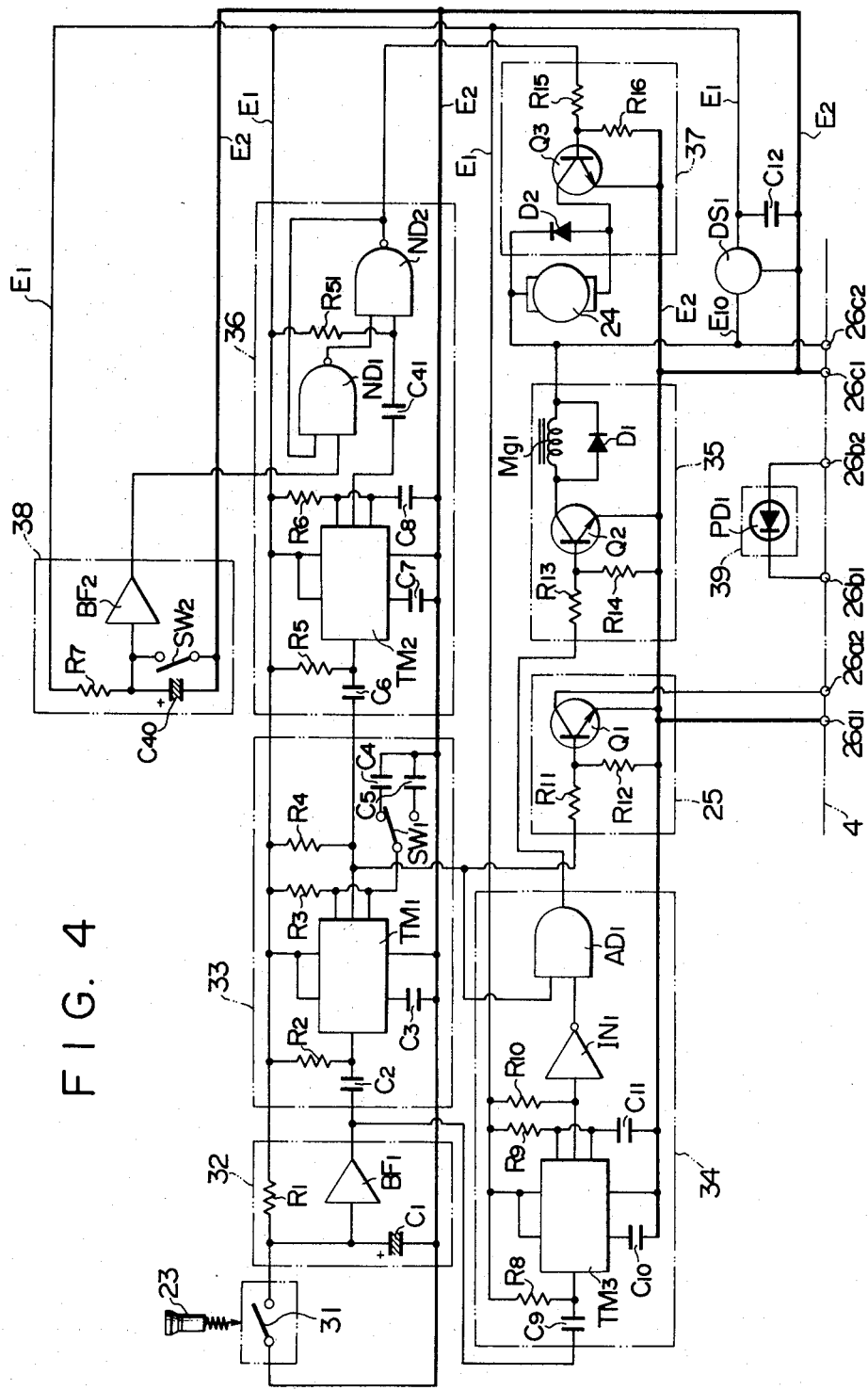
FIG. 4 is a circuit diagram of a specific form of an electrical circuit associated with the camera circuitry which is shown in FIG. 2.
Figure 5:
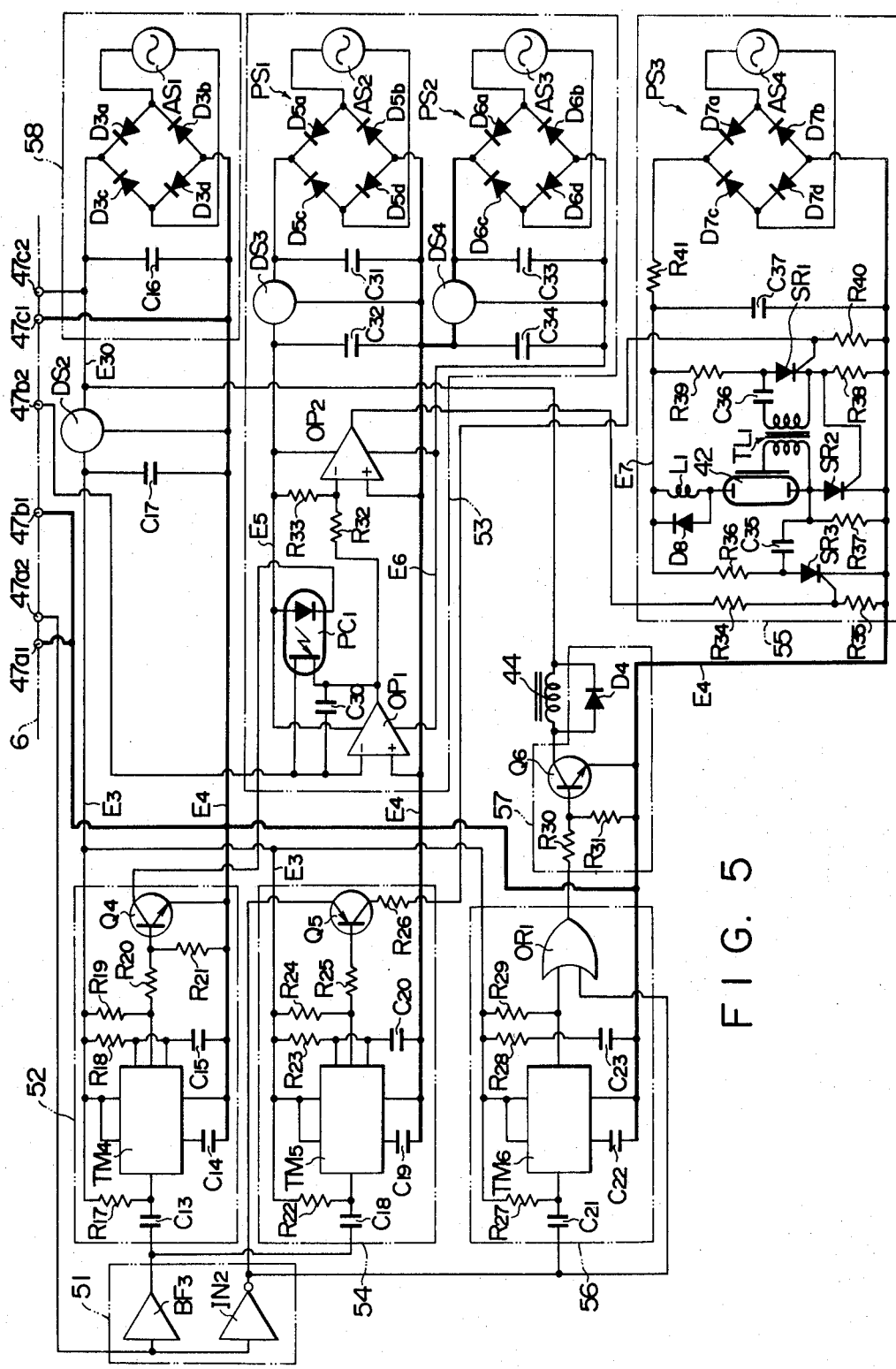
FIG. 5 is a circuit diagram of a specific form of an electrical circuit associated with the light source unit shown in FIG. 2.

FIGS. 4 and 5 show specific examples of the electrical circuit contained in the camera and the light source unit of the apparatus shown in FIG. 2.

Referring to FIG. 4, the release circuit 32 comprises resistor $R_1$, capacitor $C_1$ which serves preventing a chattering, and a waveform shaping buffer circuit $BF_1$. The resistor $R_1$ and capacitor $C_1$ are connected in series across supply buses $E_1$, $E_2$ which are in turn connected across the power supply unit 58, to be described later in connection with FIG. 5. The shutter release switch 31 is connected across the junction between the resistor $R_1$ and capacitor $C_1$ and the bus $E_2$. The junction between the resistor $R_1$ and capacitor $C_1$ is also connected to an input of the buffer circuit $BF_1$, the output of which represents the output terminal of the release circuit 32, and thus is adapted to be connected with the inputs of the succeeding shutter period presetting circuit 33 and the first delay circuit 34.

When the shutter release switch 31 is closed in response to the depression of the shutter release button 23, an "L" level input representing a close signal is applied to the buffer circuit $BF_1$ and has its waveform shaped thereby to be supplied to the succeeding circuits 33 and 34.

The shutter period presetting circuit 33 comprises timer circuit $TM_1$ which may be commercially available from Hitachi, Mfg., Co. as HA17555 or from Signetics Inc. as NE555, a shutter period changing switch $SW_1$, resistors $R_2$-$R_4$ and capacitors $C_2$-$C_5$. Timer circuit $TM_1$ is provided with eight terminals including a ground (GND), trigger, output, reset, control voltage, threshold, discharge and supply (Vcc) terminal. The input of the shutter period presetting circuit 33 is defined by one end of differentiating capacitor $C_2$, the other end of which is connected to the trigger terminal. The trigger terminal is also connected to the bus $E_1$ through differentiating resistor $R_2$ which forms a differentiator together with capacitor $C_2$. The output terminal of timer circuit $TM_1$ represents the output terminal of the shutter period presetting circuit 33 and is connected to the input of the succeeding fifth delay circuit 36, to one input of AND circuit $AD_1$ of the first delay circuit 34 and to the input of the synchronizing contact 25 which is formed by a semiconductor switching circuit, and also connected through resistor $R_4$ to the bus $E_1$. The discharge terminal is connected through timing resistor $R_3$ to the bus $E_1$, and is also connected to the threshold terminal, which is in turn connected to a movable contact of the shutter period changing switch $SW_1$ which has its one fixed contact connected through timing capacitor $C_4$ to the bus $E_2$ and its other fixed contact connected through another timing capacitor $C_5$ to the bus $E_2$. The control voltage terminal is connected through stabilizing capacitor $C_3$ to the bus $E_2$, and the reset terminal and the supply terminal are connected in common to the bus $E_1$. Finally, the ground terminal is connected to the bus $E_2$.

In operation, the circuit 33 responds to the close signal indicative of the closure of the shutter release switch 31 which is produced by the release circuit 32, by producing an "H" level output for a time interval which is determined by the time constant of the combination of resistor $R_3$ and either capacitor $C_4$ or $C_5$ which is chosen by the switch $SW_1$.

The fifth delay circuit 36 comprises timer circuit $TM_2$ which is similar to timer circuit $TM_1$, resistors $R_5$, $R_6$, $R_{51}$, capacitors $C_6$, $C_7$, $C_{41}$, and two NAND circuits $ND_1$, $ND_2$. Timer circuit $TM_2$ constitutes, together with resistors $R_5$, $R_6$ and capacitors $C_6$ to $C_8$, a monostable multivibrator which is similar to the shutter period presetting circuit 33. Its output is connected through differentiating capacitor $C_{41}$ to one input of NAND circuit $ND_2$. NAND circuits $ND_1$ and $ND_2$ constitute together a flipflop, with the output of NAND circuit $ND_1$ fed to one input of the other NAND circuit $ND_2$ and the output of NAND circuit $ND_2$ fed to one input of NAND circuit $ND_1$. The other input of NAND circuit $ND_1$ is connected to the output of the frame detector 38. Differentiating resistor $R_{51}$, which forms a stabilizing differentiator together with capacitor $C_{41}$, is connected across the other input of NAND circuit $ND_2$ and bus $E_1$.

In the operation of the fifth delay circuit 36, as the output from the shutter period presetting circuit 33 returns to an "L" level after the given time interval, timer circuit $TM_2$ produces an "H" level output for a time interval of $T_5$. When the time interval $T_5$ has passed and the output of timer circuit $TM_2$ returns to its "L" level, the flipflop is set, supplying its "H" level output to the succeeding motor drive circuit 37. The flipflop is reset to its "L" level in response to an output from the frame detector 38 to be described below.

The frame detector 38 comprises frame detecting switch $SW_2$, resistor $R_7$, capacitor $C_{40}$ which prevents a chattering, and a waveform shaping buffer circuit $BF_2$. The resistor $R_7$ and capacitor $C_{40}$ are connected in series across the buses $E_1$, $E_2$, and the junction therebetween is connected to one end of the frame detecting switch $SW_2$, the other end of which is connected to the bus $E_2$. The frame detecting switch $SW_2$ is constructed to be momentarily closed by detecting one film frame having been wound and then returns to its original position. The junction between resistor $R_7$ and capacitor $C_{40}$ is connected to the input of buffer circuit $BF_2$, the output of which is connected to the other input of NAND circuit $ND_1$ which is included in the fifth delay circuit 36.

In operation, as the frame detecting switch $SW_2$ is closed in response to a winding operation of one film frame, it produces a signal indicative of the closure, which close signal has its waveform shaped by the buffer circuit $BF_1$ before it is outputted.

The first delay circuit 34 comprises timer circuit TM$_3$ which is similar to timer circuit TM$_1$ described above, inverter IN$_1$, AND circuit AD$_1$, resistors R$_8$-R$_{10}$ and capacitors C$_9$-C$_{11}$. Together with resistors R$_8$-C$_{10}$ and capacitors C$_9$-C$_{11}$, timer circuit TM$_3$ forms a monostable multivibrator in the same manner as the shutter period presetting circuit 33, and the output of the multivibrator is connected to the input of the inverter IN$_1$. The output of inverter IN$_1$ is connected to the other input of AND circuit AD$_1$, the other input of which is connected to the output of the circuit 33 as mentioned previously. The output of AND circuit AD$_1$ represents the output of the first delay circuit 34 and is connected to the input of the succeeding shutter drive circuit 35.

In the operation of the first delay circuit 34, in response to a close signal from the shutter release switch 31 which is produced by the release circuit 32, timer circuit TM$_3$ produces an "H" level output for a time interval of T$_1$ which is determined by the combination of resistor R$_9$ and capacitor C$_{11}$. When the time interval T$_1$ passes, the output of timer circuit TM$_3$ returns to its "L" level, whereby inverter IN$_1$ feeds an "H" level signal to the succeeding shutter drive circuit 35 for a time interval during which the output of the shutter period presetting circuit 33 remains at its "H" level.

The synchronizing contact 25 comprises a semiconductor switching circuit which is formed by a switching transistor Q$_1$ associated with resistors R$_{11}$, R$_{12}$. The transistor Q$_1$ is of an NPN type, and has its base connected through resistor R$_{11}$ to the output of the circuit 33 and also connected through resistor R$_{12}$ to the bus E$_2$. The transistor Q$_1$ has its collector connected to one (26a$_2$) of a pair of synchronizing contact signal transmitting terminals 26a$_1$, 26a$_2$ which are included in the electrical terminals 26 of the camera 4, and has its emitter connected to the other terminal 26a$_1$ through the bus E$_2$.

In the operation of the synchronizing contact 25, the transistor Q$_1$ is turned on during the time the circuit 33 supplies an "H" level signal or during the given shutter period, thus short-circuiting the path across the terminals 26a$_1$, 26a$_2$.

The shutter drive circuit 35 comprises an electromagnet Mg$_1$ which is used to drive the mirror shutter 20 for upward movement, transistor Q$_2$ which controls the energization of the electromagnet Mg$_1$, a diode D$_1$ which serves suppressing a counter electromotive force developed across the electromagnet when it is deenergized, and resistors R$_{13}$, R$_{14}$. The transistor Q$_2$ is of an NPN type, and has its base connected through resistor R$_{13}$ to the output of the first delay circuit 34, and also connected through resistor R$_{14}$ to the bus E$_2$. The transistor Q$_2$ has its collector connected through the electromagnet Mg$_1$ to a supply bus E$_{10}$ which is in turn connected to the power supply unit 58, and its emitter connected to the bus E$_2$. It will be noted that diode D$_1$ is connected in shunt with the electromagnet Mg$_1$ and is poled reversely with respect to the drive current through the electromagnet.

In operation, the transistor Q$_2$ is turned on in response to an "H" level output from the first delay circuit 34, thereby energizing the electromagnet Mg$_1$ to drive the mirror shutter 20 for an upward movement.

The motor drive circuit 37 comprises a transistor Q$_3$ which controls a drive to the film winding motor 24, a diode D$_2$ connected across and reversely poled with respect to the motor 24, and resistors R$_{15}$, R$_{16}$. The transistor Q$_3$ is of an NPN type, and has its base connected through resistor R$_{15}$ to the output of the fifth delay circuit 36, and also connected through resistor R$_{16}$ to the bus E$_2$. The transistor Q$_3$ has its collector connected through the film winding motor 24 to the bus E$_{10}$ and has its emitter connected to the bus E$_2$.

It will be noted that the transistor Q$_3$ is turned on in response to an output from the fifth delay circuit 36, thereby driving the motor 24 for rotation.

The automatic exposure controlling, photometric circuit 39 comprises a photodiode PD$_1$, the opposite ends of which are connected to photometric signal transmitting terminals 26b$_1$, 26b$_2$, which are included in the electrical terminals 26 of the camera. It will be appreciated that the photometric circuit 39 develops a photocurrent in accordance with the amount of light from an object being photographed which is incident into the camera 4, supplying a photometric signal to the light source unit 6 through the terminals 26b$_1$, 26b$_2$.

The pair of buses E$_{10}$ and E$_2$ are connected to a pair of power terminals 26c$_1$, 26c$_2$ which are included in the electrical terminals 26, so that the electromagnet Mg$_1$ and the motor 24 can be fed from the power supply unit 58 which will be described later in connection with FIG. 5. The bus E$_1$ is connected to the bus E$_{10}$ through a d.c. stabilizing power supply circuit DS$_1$ which is formed by an integrating circuit of well known form. The power supply circuit DS$_1$ maintains a constant output voltage, for example, of 5 V, irrespective of any variation in the input voltage. It will be seen that its input is connected to the bus E$_{10}$ while its output is connected to the bus E$_1$. The ground terminal of the circuit DS$_1$ is connected to the bus E$_2$, with smoothing capacitor C$_{12}$ connected across the output and the ground terminal.

Referring to FIG. 5 which illustrates a specific form of the electrical circuit contained in the light source unit 6, the sequence control circuit 51 comprises a buffer circuit BF$_3$ and inverter IN$_2$, both of which have their input connected to a synchronizing contact signal transmitting terminal 47a$_2$ which is included in the electrical terminals 47 of the light source unit 6. The output of buffer circuit BF$_3$ is connected to the input of the second and the third delay circuit 52, 54, respectively, while the output of inverter IN$_2$ is connected to the collector of transistor Q$_5$ contained in the third delay circuit 54, to the input of the fourth delay circuit 56 and to one input of OR circuit OR$_1$ which is contained in the fourth delay circuit 56.

The purpose of the sequence control circuit 51 is to provide a waveform shaping of synchronizing contact signal which is supplied from the terminal 47a$_2$ and to convert it into a pair of signals of opposite polarities.

The second delay circuit 52 comprises timer circuit TM$_4$ which is similar to timer circuit TM$_1$ mentioned above in connection with the shutter period presetting circuit 33 of the camera 4, a transistor Q$_4$ which controls a drive to a photocoupler PC$_1$ to be described later, resistors R$_{17}$-R$_{21}$ and capacitors C$_{13}$-C$_{15}$. Together with resistors R$_{17}$-R$_{19}$ and capacitors C$_{13}$-C$_{15}$, timer circuit TM$_4$ forms a monostable multivibrator in the same manner as the circuit 33, and is connected across a pair of supply buses E$_3$, E$_4$ which are derived from the power supply unit 58 to be described later. The input of the second delay circuit 52 is defined by one end of differentiating capacitor C$_{13}$, the other end of which is connected to the input of the timer circuit TM$_4$. The output of timer circuit TM$_4$ is connected through resistor $R_{20}$ to the base of transistor $Q_4$. The transistor $Q_4$ is of an NPN type, and has its base connected through bias resistor $R_{21}$ to the bus $E_4$. The transistor $Q_4$ has its collector connected to the cathode of a light emitting element of the photocoupler $PC_1$, and its emitter connected to the bus $E_4$.

In the operation of the second delay circuit 52, it receives a close signal indicative of the closure of the synchronizing contact 25 from the sequence control circuit 51 to activate timer circuit $TM_4$, whereby transistor $Q_4$ is turned on for a time interval of $T_2$, thereby conditioning the exposure calculation circuit 53 to be ready to initiate its operation.

The power supply unit 58 comprises an a.c. power source $AS_1$, four rectifying diodes $D_{3a}$–$D_{3d}$, and smoothing capacitor $C_{16}$. The four rectifying diodes $D_{3a}$–$D_{3d}$ are arranged in a bridge configuration, thus forming a single phase full wave rectifier. The a.c. source $AS_1$ is connected across the junction between diodes $D_{3a}$, $D_{3b}$ and the junction between diodes $D_{3c}$, $D_{3d}$ while the junction between diodes $D_{3a}$, $D_{3c}$ and the junction between diodes $D_{3b}$, $D_{3d}$ are connected to a bus $E_{30}$ and the bus $E_4$, respectively. Capacitor $C_{16}$ is connected across the buses $E_{30}$, $E_4$. The bus $E_{30}$ is connected to a feed terminal $47c_2$ which is included in the electrical terminals 47, and also to the electromagnet 44 as well as the input of a d.c. stabilizing power supply circuit $DS_2$ of a known form which is formed by an integrated circuit. The bus $E_4$ is connected to another feed terminal $47c_1$. The power supply circuit $DS_2$ has its output connected to the bus $E_3$ and its ground terminal connected to the bus $E_4$, with smoothing capacitor $C_{17}$ connected across the buses $E_3$, $E_4$.

In the operation of the power supply circuit 58, it converse an alternating current from the a.c. source $AS_1$ into a direct current which is fed to the individual electrical circuits of the camera 4 through the terminals $47c_1$, $47c_2$ and which is also fed to the sequence control circuit 51, the second to the fourth delay circuit 52, 54, 56 through the d.c. stabilizing power supply circuit $DS_2$. The power supply circuit 58 also feeds the electromagnet 44.

The third delay circuit 54 comprises timer circuit $TM_5$ which is similar to timer circuit $TM_1$ mentioned previously, a switching transistor $Q_5$ which triggers the emission of light from the photographing light source 42, resistors $R_{22}$–$R_{26}$ and capacitors $C_{18}$–$C_{20}$. Together with resistors $R_{22}$–$R_{24}$ and capacitors $C_{18}$–$C_{20}$, timer circuit $TM_5$ forms a monostable multivibrator in the same manner as the circuit 33, and is connected across the buses $E_3$, $E_4$. The output of timer circuit $TM_5$ is connected through resistor $R_{25}$ to the base of transistor $Q_5$. The transistor $Q_5$ is of a PNP type, and has its emitter connected to the output of inverter $IN_2$ which is included in the sequence control circuit 51, and has its collector connected through resistor $R_{26}$ to the gate of thyristor $SR_1$ which acts as a trigger switch to initiate the emission of light from the photographing light source control circuit 55 to be described later.

In the operation of the third delay circuit 54, in response to a close signal indicative of the closure of the synchronizing contact 25 which is fed from the sequence control circuit 51, timer circuit $TM_5$ is activated to produce an "H" level output for a time interval of $T_3$. Subsequently its output returns to an "L" level, whereupon transistor $Q_5$ is turned on to trigger thyristor $SR_1$.

The fourth delay circuit 56 comprises timer circuit $TM_6$ which is similar to timer circuit $TM_1$ mentioned previously, OR circuit $OR_1$, resistors $R_{27}$–$R_{29}$ and capacitors $C_{21}$–$C_{23}$. Together with resistors $R_{27}$–$R_{29}$ and capacitors $C_{21}$–$C_{23}$, timer circuit $TM_6$ forms a monostable multivibrator, and has its input connected to one end of differentiating capacitor $C_{21}$, the other end of which represents the input of the fourth delay circuit 56. The output of timer circuit $TM_6$ is connected to one input of OR circuit $OR_1$, the other input of which is connected to the output of inverter $IN_2$. The output of OR circuit $OR_1$ is connected to the input of the electromagnet drive circuit 57.

In the operation of the first delay circuit 56, it maintains the output fed to the electromagnet drive circuit 57 for a time interval $T_4$ even after the given shutter period has passed, thereby delaying a returning movement of the reflecting mirror 43 onto the light path.

The electromagnet drive circuit 57 comprises transistor $Q_6$ which controls a drive to the electromagnet 44, diode $D_4$ connected in shunt with and poled reversely with respect to the current flow through the electromagnet 44 in order to suppress a counter electromotive force developed thereacross upon deenergization thereof, and resistors $R_{30}$, $R_{31}$. The transistor $Q_6$ is of an NPN type, and has its base connected through resistor $R_{30}$ to the output of OR circuit $OR_1$ and also connected through bias resistor $R_{31}$ to the bus $E_4$. The transistor $Q_6$ has its collector connected through the electromagnet 44 to the bus $E_{30}$, and has its emitter connected to the bus $E_4$.

It will be noted that the transistor $Q_6$ is turned on in response to an output from the fourth delay circuit 56, thereby driving the electromagnet 44.

The exposure calculation circuit 53 comprises an integrating operational amplifier $OP_1$, integrating capacitor $C_{30}$, photocoupler $PC_1$ which is used to reset the integrating circuit, comparison operational amplifier $OP_2$, resistors $R_{32}$, $R_{33}$, and positive and negative power supplies $PS_1$, $PS_2$. The positive power supply $PS_1$ is formed by an a.c. power source $AS_2$, four rectifying diodes $D_{5a}$–$D_{5d}$ which are arranged in a bridge configuration, a d.c. stabilizing power supply circuit $DS_3$, and a pair of smoothing capacitors $C_{31}$, $C_{32}$. The negative power supply $PS_2$ is constructed in the same manner as the positive power supply $PS_1$, and is formed by an a.c. power source $AS_3$, rectifying diodes $D_{6a}$–$D_{6d}$, d.c. stabilizing power supply circuit $DS_4$ and smoothing capacitors $C_{33}$, $C_{34}$.

In the positive power supply $PS_1$, the four diodes $D_{5a}$–$D_{5d}$ and capacitor $C_{31}$ form a single phase full wave rectifier in the same manner as the power supply unit 58, with its positive output line connected to the input of the d.c. stabilizing power supply circuit $DS_3$, the output of which is connected to a supply bus $E_5$. The negative output line of the rectifier is connected to the bus $E_4$, with capacitor $C_{31}$ connected across the positive and the negative output line and another capacitor $C_{32}$ connected across the buses $E_5$, $E_4$. It is to be noted that the ground terminal of the d.c. stabilizing power supply circuit $DS_3$ is connected to the bus $E_4$. The negative power supply $PS_3$ is connected in the same manner as the positive power supply $PS_1$, with a positive output line of the full wave rectifier connected to the input of the d.c. stabilizing power supply circuit $PS_4$, the output of which is connected to the bus $E_4$. The negative output line of the full wave rectifier is connected to a supply bus $E_6$.

The integrating operational amplifier $OP_1$ is connected across the buses $E_5$, $E_6$, and has its inverting input connected to a photometric signal transmitting terminal $47b_2$ which is included in the electrical terminals 47, and has its non-inverting input connected to the bus $E_4$. The output of the amplifier $OP_1$ is connected through resistor $R_{32}$ to the inverting input of the comparison operational amplifier $OP_2$. The integrating capacitor $C_{30}$ and the light receiving element of the photocoupler $PC_1$ are connected in shunt with each other across the output and the inverting input of the operational amplifier $OP_1$. The photocoupler $PC_1$ includes a light emitting element which has its anode connected to the bus $E_5$ and which has its cathode connected to the collector of transistor $Q_4$. The operational amplifier $OP_2$ is connected across the supply buses $E_5$, $E_6$, with its inverting input connected through resistor $R_{33}$ to the bus $E_5$. The non-inverting input of the operational amplifier $OP_2$ is connected to the bus $E_4$, while its output is connected through resistor $R_{34}$ to the gate of thyristor $SR_3$ which operates as a trigger switch associated with the photographing light source control circuit 55 for interrupting the emission of light therefrom.

In the operation of the exposure calculation circuit 53 thus constructed, when transistor $Q_4$ in the second delay circuit 52 is turned on to drive the photocoupler $PC_1$, capacitor $C_{30}$ is short-circuited, whereby the integrating circuit is reset. When transistor $Q_4$ is turned off, the photocoupler $PC_1$ ceases to be driven. In this manner, an integration of a photometric signal from the photometric circuit 39 is initiated. When the integrated voltage reaches a given value, the operational amplifier $OP_2$ which operates as a level detector has its output reversed, thus firing thyristor $SR_3$.

The photographing power source control circuit 55 is formed as an illumination control circuit of an electronic flash which is known in itself, and the photographing light source 42 is formed by a flash discharge tube which is also known. Specifically, the circuit 55 comprises a power supply $PS_3$, main capacitor $C_{37}$, thyristor $SR_1$ which operates as a trigger switch to initiate the emission of light, trigger capacitor $C_{36}$, trigger transformer $TL_1$, thyristor $SR_2$ which serves as a main switching element, coil $L_1$ shunted by diode $D_8$ which acts to suppress a counter electromotive force developed, commutating capacitor $C_{35}$, thyristor $SR_3$ which operates as a trigger switch to interrupt the emission of light, and resistors $R_{34}$–$R_{41}$. The power supply $PS_3$ is formed by an a.c. power source $AS_4$ and four rectifying diodes $D_{7a}$–$D_{7d}$.

As in the power supply unit 58, the four rectifying diodes $D_{7a}$–$D_{7d}$ are arranged in a bridge configuration to form a single phase full wave rectifier connected to the a.c. source $AS_4$. A supply bus $E_7$ is connected through resistor $R_{41}$ to the positive output terminal of the full wave rectifier while the negative output terminal is connected to the bus $E_4$. Connected across the buses $E_7$, $E_4$ are main capacitor $C_{37}$; a series circuit including resistor $R_{39}$, thyristor $SR_1$ and resistor $R_{38}$; another series circuit including a parallel combination of coil $L_1$ and diode $D_8$, light source 42 and thyristor $SR_2$; and a further series circuit including resistor $R_{36}$ and thyristor $SR_3$. The trigger transformer $TL_1$ includes a primary coil which is connected through trigger capacitor $C_{36}$ across the anode and cathode of thyristor $SR_1$, the gate of which is connected through resistor $R_{40}$ to the bus $E_4$ and also connected through resistor $R_{26}$ to the collector of transistor $Q_5$. The transformer $TL_1$ also includes a secondary coil, one end of which is connected to the trigger electrode of the light source 42 and the other end of which is connected to the cathode electrode thereof. The thyristor $SR_2$ has its anode connected to the light source 42, its cathode connected to the bus $E_4$, and its gate connected to the cathode of thyristor $SR_1$. Resistor $R_{37}$ is connected across the anode and cathode of thyristor $SR_2$. The anode of thyristor $SR_3$ is connected with one end of resistor $R_{36}$, and also connected through commutating capacitor $C_{35}$ to the anode of thyristor $SR_2$. The gate of thyristor $SR_3$ is connected through resistor $R_{35}$ to the bus $E_4$ and also connected through resistor $R_{34}$ to the output of the operational amplifier $OP_2$.

The photographing light source control circuit 55 represents an illumination control circuit of series controlled type, and when transistor $Q_5$ in the third delay circuit 54 is turned on, thyristor $SR_1$ is triggered into conduction. When thyristor $SR_1$ is fired, the trigger capacitor $C_{36}$ becomes short-circuited, thereby developing a high voltage across the secondary coil of the trigger transformer $TL_1$ to trigger thyristor $SR_2$ into conduction. In this manner, the light source 42 which is formed by a flash discharge tube initiates to emit flashlight. When a proper exposure has been given to the film surface, the output of the exposure calculation circuit 53 reverses to its "H" level, whereby thyristor $SR_3$ is triggered into conduction to short-circuit the commutating capacitor $C_{35}$. This biases the anode of thyristor $SR_2$ to the negative, whereby it is rendered non-conductive to terminate the discharge of the light source 42 which emitted the flashlight.

It is to be noted that the synchronizing contact signal transmitting terminal $47a_1$ and a photometric signal transmitting terminal $47b_1$ which are included in the electrical terminals 47 are connected to the bus $E_4$.

The synchronizing contact signal transmitting terminals $26a_1$, $26a_2$, photometric signal transmitting terminals $26b_1$, $26b_2$ and the power terminals $26c_1$, $26c_2$ which are included as the electrical terminals 26 of the camera 4 correspond to the synchronizing contact signal transmitting terminals $47a_1$, $47a_2$, the photometric signal transmitting terminals $47b_1$, $47b_2$ and the feed terminals $47c_1$, $47c_2$ which are included as the electrical terminals 47 of the light source unit 6, respectively, and are connected to the latter through the endoscope 2.

The operation of the specific electrical circuits of the camera 4 and the light source unit 6 will now be briefly described in connection with an operation of the apparatus 1.

When the shutter release button 23 of the camera 4 is depressed, the shutter release switch 31 is closed, and the release circuit 32 develops an "L" level, trigger signal which is applied to the shutter period presetting circuit 33 and the first delay circuit 34. In response thereto, the circuit 33 causes timer circuit $TM_1$ to produce an "H" level output, which turns transistor $Q_1$ on, which represents the synchronizing contact 25. When the signal indicative of the conduction of transistor $Q_1$ is developed, the sequence control circuit 51 of the light source unit 6 applies an "L" level, trigger signal to the second and the third delay circuit 52 and 54 and also applies an "H" level signal to the transistor $Q_5$ of the third delay circuit 54 and to the fourth delay circuit 56. As a consequence, in the second timer circuit 52, timer circuit $TM_4$ produces an "H" level output, which turns transistor $Q_4$ on, thus driving the photocoupler $PC_1$ of the exposure calculation circuit 53 to reset the integrating circuit formed by the operational amplifier $OP_1$ and capacitor $C_{30}$. In the third delay circuit 54, the transistor $Q_5$ begins to be fed, but since timer circuit $TM_5$ produces an "H" level output simultaneously, the transistor $Q_5$ is not turned on to supply an output to the photographing light source control circuit 55. In the fourth delay circuit 56, OR circuit $OR_1$ is enabled, whereby transistor $Q_6$ in the electromagnet drive circuit 57 is turned on to energize the electromagnet 44, moving the reflecting mirror 43 out of the light path. On the other hand, in the first delay circuit 34, the "L" level signal from the release circuit 32 causes timer $TM_3$ to produce an "H" level output, thus initiating a time delay of $T_1$.

After the time delay $T_1$ has passed, timer circuit $TM_3$ in the first delay circuit 34 reverts its output to an "L" level, whereby AND circuit $AD_1$ is enabled by the output from inverter $IN_1$ and timer circuit $TM_1$, producing an "H" level output. In response thereto, transistor $Q_2$ in the shutter drive circuit 35 is turned on to energize the electromagnet $Mg_1$, whereby the mirror shutter 20 is driven for movement out of the taking light path.

Subsequently, when the time interval $T_2$ has passed, timer $TM_4$ in the second delay circuit 52 reverts its output to an "L" level. Thereupon, transistor $Q_4$ is turned off, thereby ceasing to drive the photocoupler $PC_1$. Consequently, an integration of a photometric signal from the photometric circuit 39 is initiated by the integrating circuit formed by the operational amplifier $OP_1$ and capacitor $C_{30}$.

Subsequently, after the time interval $T_3$ passes, timer circuit $TM_5$ in the third delay circuit 54 has its output reversed to an "L" level. Transistor $Q_5$ is then turned on to trigger the thyristor $SR_1$ in the photographing light source control circuit 55 into conduction. When thyristor $SR_1$ is triggered into conduction, the charge on the trigger capacitor $C_{36}$ causes a current flow through the primary coil of trigger transformer $TL_1$, inducing a high voltage across the secondary coil thereof, and thyristor $SR_2$ is also fired, whereby the photographing light source 42 begins to produce the flashlight.

In the exposure calculation circuit 53, the integrating circuit formed by the operational amplifier $OP_1$ and capacitor $C_{30}$ integrates a photometric signal, and when an integrated voltage reaches a given value, the output of operational amplifier $OP_2$ is reversed to an "H" level. Thereupon, thyristor $SR_3$ in the control circuit 55 is triggered into condition, short-circuiting the commutating capacitor $C_{35}$. As a result, thyristor $SR_2$ is reverse biased to be rendered non-conductive, and hence the light source 42 ceases to produce the flashlight.

Then, when the shutter period has passed, timer circuit $TM_1$ in the shutter period presetting circuit 33 has its output reverted to an "L" level, whereby the output of AND circuit $AD_1$ in the first delay circuit 34 returns to an "L" level to turn transistor $Q_2$ in the shutter drive circuit 35 off, thus deenergizing the electromagnet $Mg_1$. Consequently, the mirror shutter 20 returns to its position on the taking light path. Also, transistor $Q_1$ which constitutes the synchronizing contact 25 is turned off, and a corresponding signal is fed through the sequence control circuit 51 to be applied as an "H" level signal to the second and the third delay circuit 52, 54, and also applied as an "L" level signal to the emitter of transistor $Q_5$ in the second delay circuit 52 and to the fourth delay circuit 56. Therefore, the second and the third delay circuit 52, 54 return to their initial condition. In the fourth delay circuit 56, timer circuit $TM_6$ initiates its delaying operation, changing its output to an "H" level to maintain the electromagnet 44 energized. On the other hand, in response to an "L" level signal from timer circuit $TM_1$ in the shutter period presetting circuit 33, timer circuit $TM_2$ in the fifth delay circuit 35 changes its output to an "H" level. However, no change is produced in the flipflop formed by NAND circuits $ND_1$, $ND_2$, and hence the output of the fifth delay circuit 36 is maintained at an "L" level.

When the time interval $T_4$ passes after the expiration of the preset shutter period, timer circuit $TM_6$ in the fourth delay circuit 56 has its input reverted to an "L" level, whereby the output of OR circuit $OR_1$ changes to an "L" level, turning transistor $Q_6$ in the electromagnet drive circuit 57 off to deenergize the electromagnet 44, allowing the reflecting mirror 43 to be returned to its normal position.

When the time interval $T_5$ has passed since the expiration of the preset shutter period, timer circuit $TM_2$ in the fifth delay circuit 36 has its input reverted to an "L" level, whereby flipflop formed by NAND circuits $ND_1$, $ND_2$ is set, producing an "H" level output from the fifth delay circuit 36. In response thereto, transistor $Q_3$ in the motor drive circuit 37 is turned on to energize the motor 24, thus initiating a film winding operation.

When one exposed film frame has been wound up, the frame detecting switch $SW_2$ of the frame detector 38 is closed, whereby the detector 38 applies an "L" level signal to NAND circuit $ND_1$ of the fifth delay circuit 36. Thereupon, the flipflop formed by NAND circuits $ND_1$, $ND_2$ is reset, changing the output from the fifth delay circuit 36 to an "L" level. Hence, transistor $Q_6$ in the motor drive circuit 37 is turned off, ceasing the rotation of the motor 24. This completes the film winding operation.

The above description covers a series of operations involved with a single photographing operation with the apparatus 1 which are controlled by the specific electrical circuits of the camera 4 and the light source unit 6 mentioned above.

Figure 6:
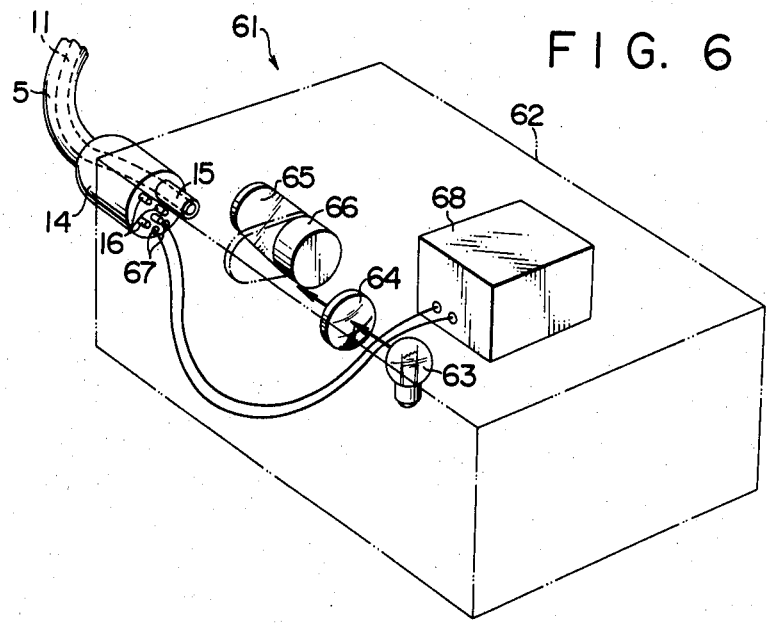
FIG. 6 is a perspective view of the light source unit of an apparatus for endoscopic photography according to another embodiment of the invention.

FIG. 6 shows a light source unit 62 associated with an apparatus for endoscopic photography 61 according to another embodiment of the invention. The apparatus 61 is constructed in the same manner as the apparatus 1 shown in FIG. 1 except for the arrangement of the light source unit 62. Hence, only the light source unit 62 will be described specifically, and the remainder of the apparatus will not be described.

The light source unit 62 is arranged to supply both the diagnostic light and the photographing light. It comprises a light 63, a condenser lens 64 disposed in a light path extending from the light 63 to the light guide connector 15 of the endoscope 2, and a light shield member 65 movably disposed so as to intercept a light path between the light 63 and the light guide connector 15. An electromagnet 66 is associated with the light shield member 65 to drive it, and an automatic exposure control circuit 88 is connected to electrical terminals 64, which are adapted to mate with the electrical terminals 16 of the endoscope for receiving various electrical signals from camera 4.

Figure 7:
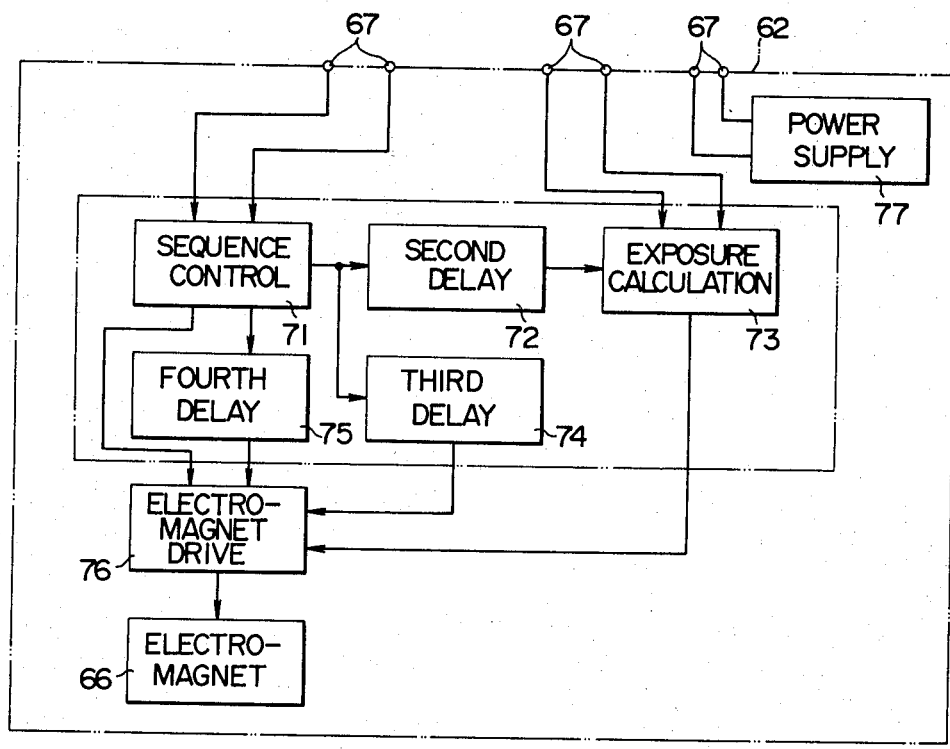
FIG. 7 is a block diagram of an electrical circuit contained in the light source unit shown in FIG. 6.

FIG. 7 shows the electrical circuit of the automatic exposure control circuit 68. Specifically, the circuit 68 comprises a sequence control circuit 71 which is connected to the synchronizing contact 25 of the camera 4 through the electrical terminals 67. A second delay circuit 72 receives an output from the sequence control circuit 71 as an input and becomes operative after the mirror shutter 20 has been fully opened. An exposure calculation circuit 73 is responsive to an output from the second delay circuit for initiating a calculation of the amount of exposure in accordance with a signal from the photometric circuit 39 of the camera 4. third delay circuit 74 receives an output from the sequence control circuit 71 as an input and becomes operative after the exposure calculation circuit 73 has initiated its operation. A fourth delay circuit 75 is rendered operative by an open signal indicative of the opening of the synchronizing contact 25 which is produced by the sequence control circuit 71 for ceasing to produce an output upon completion of the closure of the mirror shutter 20, and a power supply unit 77 is responsive to outputs from the sequence control circuit 71, the third delay circuit 74, the exposure calculation circuit 73 and the fourth delay circuit 75 for feeding an electromagnet drive circuit 76 directly and for feeding the shutter drive circuit 35 and the motor drive circuit 37 of the camera 4 through the electrical terminals 67. The electromagnet 66 operates to bring the light shield member 65 to its closed, open, closed and open positions in a sequential manner. While not shown, the light 63 is fed from the power supply unit 77 in the same manner as the diagnostic light source 41, and normally remains in its illuminating condition whenever a main switch (not shown) of the light source unit 62 is turned on.

The operation of the apparatus 61 is substantially similar to that of the apparatus 1 shown in FIGS. 1 to 3, and hence will be briefly described with reference to FIG. 8.

Figure 8:
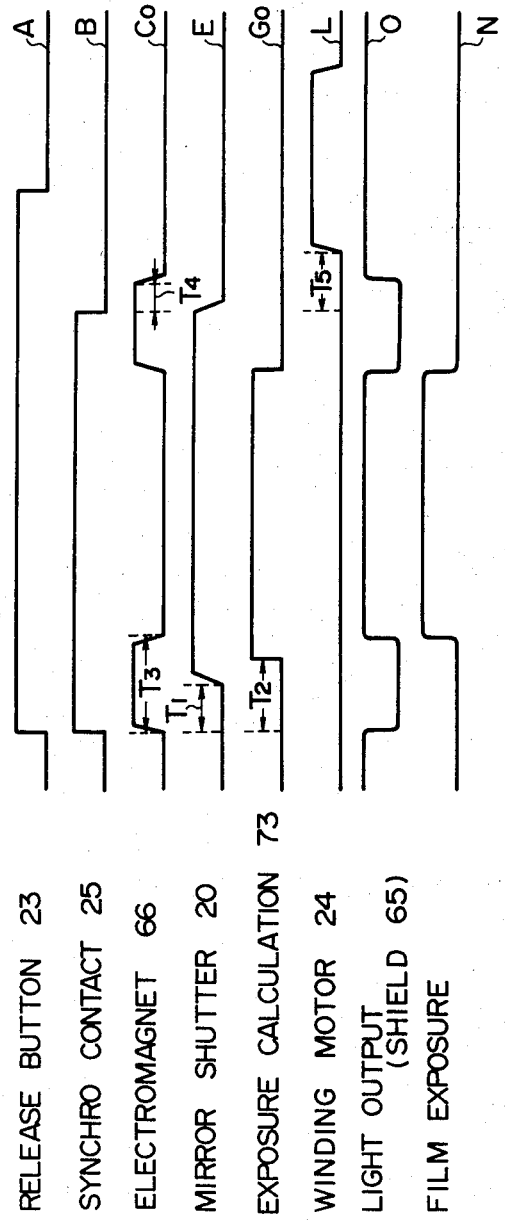
FIG. 8 is a timing chart illustrating the various timings of operation of the apparatus which utilizes the light source unit shown in FIG. 7.

Initially, when the release button 23 is depressed as illustrated by graph A of FIG. 8, the synchronizing contact 25 is closed as indicated by graph B of FIG. 8. A close signal indicative of the closure of the synchronizing contact 25 is fed through the sequence control circuit 71 to the electromagnet drive circuit 76, whereby the electromagnet 66 is energized as indicated by graph $C_0$ of FIG. 8. Hence, the light shield member 65 is brought onto the light path as indicated by graph D of FIG. 8, intercepting the light which is incident into the camera 4.

Subsequently, after a time delay $T_1$ determined by the fourth delay circuit 34 and which is sufficient to bring the light shield member 65 to its closed position subsequent to the depression of the release button 23, the mirror shutter 20 is opened, as indicated by graph E of FIG. 8. Subsequently, after a time delay $T_2$ determined by the second delay circuit 72 and which is sufficient to allow the mirror shutter 20 to be fully opened in response to the closure of the synchronizing contact 25, the exposure calculation circuit 73 initiates its operation, as indicated by graph $G_0$ of FIG. 8. Subsequently, after a time delay $T_3$ determined by the third delay circuit 74 and which is sufficient to allow the exposure calculation circuit 73 to initiate its operation subsequent to the closure of the synchronizing contact 25, the electromagnet 66 ceases to be energized, as indicated by graph $C_0$ of FIG. 8, whereby the light shield member 65 is moved out of the light path, as indicated by graph D of FIG. 8. The light from the light 65 is then directed through the endoscope 2 and reflected by the internal wall of a coeliac cavity to be incident into the camera 4, whereby it is focussed onto a film surface for exposure as indicated by graph N of FIG. 8. It is to be understood that the brightness of the light 63 may be temporarily increased.

As the exposure of the film surface continues and a proper exposure is reached, the exposure calculation circuit 73 ceases to produce its output, as indicated by graph $G_0$ of FIG. 8, whereupon the electromagnet 66 is energized again as indicated by graph $C_0$, thus bringing the light shield member 65 to its light path intercepting position.

Subsequently, the shutter period presetting circuit 33 becomes inoperative after the preset time interval to open the synchronizing contact 25 as indicated by graph B, whereby the fourth delay circuit 75 responds thereto to deenergize the electromagnet 66 after a time delay $T_4$. Consequently, the light shield member 65 is moved out of the light path, permitting an incidence of the diagnostic light into the camera 4 again. After a time interval $T_5$ which is sufficient to allow the mirror shutter 20 to be fully closed subsequent to the opening of the synchronizing contact 25, the fifth delay circuit 36 operates the motor 24 to effect a film winding operation, as indicated by graph L. This film winding operation is detected by the frame detector 38, and the motor 24 comes to a stop after one exposed film frame has been wound up.

In this manner, a picture is taken on one film frame. It is to be noted that the film surface is exposed only to photographing light when the apparatus 61 is used, in the same manner as the apparatus 1 is used, and the exposure is accurately controlled by the exposure calculation circuit 73. In this manner an automatic exposure control with a high accuracy is achieved.

Figure 9:
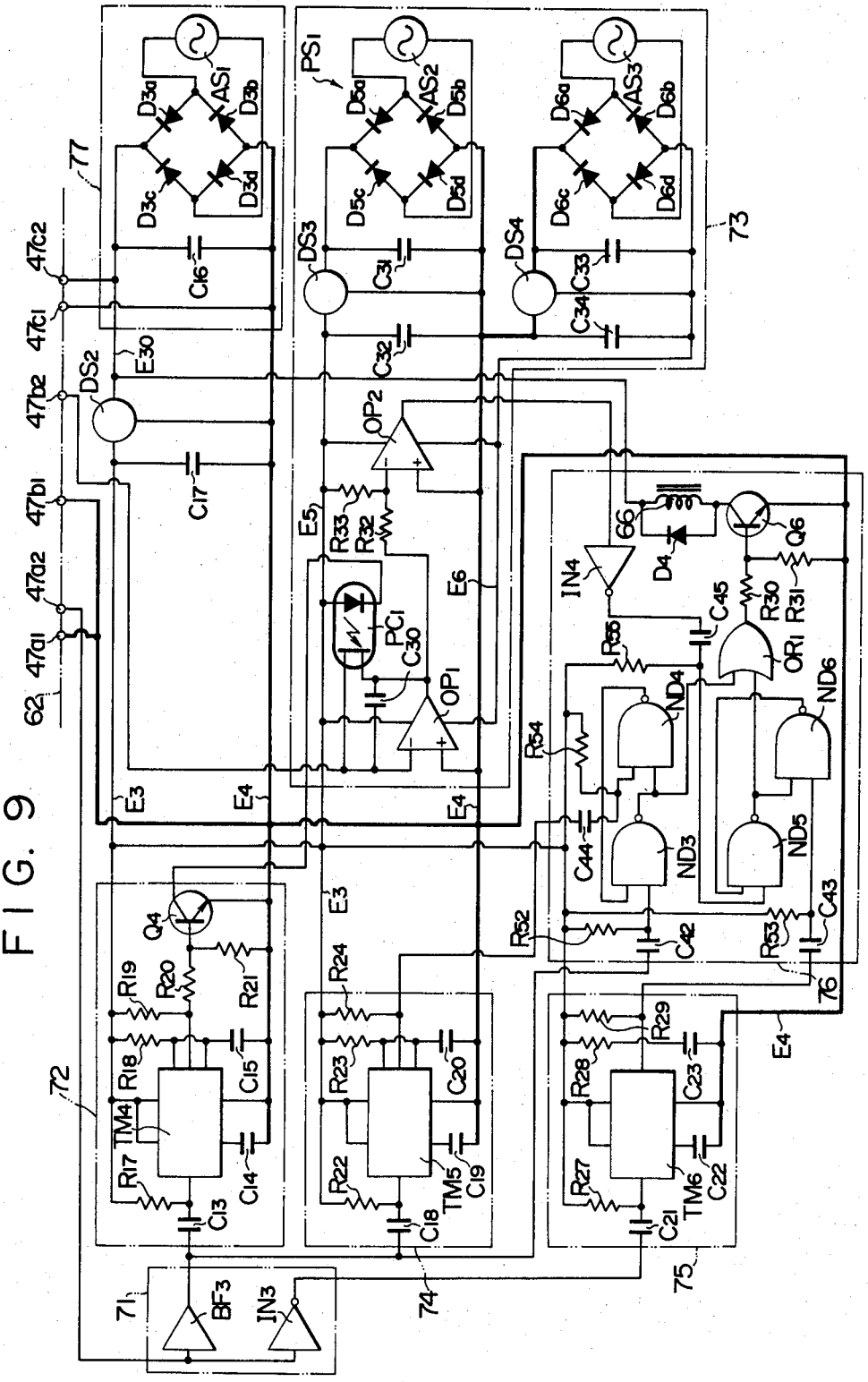
FIG. 9 is a circuit diagram of a specific form of the electrical circuit of the light source unit shown in FIG. 7.

FIG. 9 shows a specific form of the electrical circuit of the light source unit 62 shown in FIG. 7. In this Figure, the sequence control circuit 71, the second delay circuit 72, the exposure calculation circuit 73 and the power supply unit 77 correspond to and are constructed in identical manners as the sequence control circuit 51, the second delay circuit 52, the exposure calculation circuit 53 and the power supply unit 58, respectively, shown in FIG. 5, and hence corresponding parts are designated by like reference characters without repeating their description. In the remainder of the circuit, certain components and circuits are constructed in the same manner as those shown in the electrical circuit of FIG. 5, and therefore will be designated by like reference characters without specifically referring thereto.

The third delay circuit 74 comprises a monostable multivibrator which is formed by timer circuit $TM_4$ in combination with resistors $R_{22}$–$R_{24}$ and capacitors $C_{18}$–$C_{20}$. The input of the third delay circuit 74 is connected to the output of the buffer circuit $BF_3$ in the sequence control circuit 71, and the output of the third delay circuit 74 is connected to one input of NAND circuit $ND_4$ in the electromagnet drive circuit 76. Similarly, the fourth delay circuit 75 comprises a monostable multivibrator which is formed by timer circuit $TM_6$ in combination with resistors $R_{27}$–$R_{29}$ and capacitors $C_{21}$–$C_{23}$. Its input is connected to the output of inverter $IN_3$ in the sequence control circuit 71 while its output is connected to one input of NAND circuit $ND_6$ in the electromagnet drive circuit 76.

The electromagnet drive control circuit 76 comprises four NAND circuits $ND_3$–$ND_6$, OR circuit $OR_1$, inverter $IN_4$, transistor $Q_6$ which controls a drive to the electromagnet 66, capacitors $C_{42}$–$C_{45}$, resistors $R_{30}$, $R_{31}$ and $R_{52}$–$R_{55}$, and diode $D_4$ which is connected in shunt with the electromagnet 66 to suppress a counter electromotive force developed thereacross upon deenergization thereof. NAND circuits $ND_3$ and $ND_4$ form together a flipflop. Specifically, one input of NAND circuit $ND_3$ is connected to the output of NAND circuit $ND_4$, and the output of NAND circuit $ND_3$ is connected to the other input of NAND circuit $ND_4$. The other input of NAND circuit $ND_3$ is connected through differentiating capacitor $C_{42}$ to the output of the buffer circuit $BF_3$. The one input of NAND circuit $ND_4$ is connected through differentiating capacitor $C_{44}$ to the output of the third delay circuit 74. In the same manner, NAND circuits $ND_5$ and $ND_6$ also form together a flipflop. Specifically, one input of NAND circuit $ND_5$ is connected to the output of NAND circuit $ND_6$, and the output of NAND circuit $ND_5$ is connected to one input of NAND circuit $ND_6$. The other input of NAND circuit $ND_5$ is connected through differentiating capacitor $C_{45}$ and inverter $IN_4$ to the output of the operational amplifier $OP_2$ in the exposure calculation circuit 73 while the other input of NAND circuit $ND_6$ is connected through differentiating capacitor $C_{43}$ to the output of the fourth delay circuit 75. Additionally, the output of NAND circuit $ND_3$ is connected to one input of OR circuit $OR_1$, the other input of which is connected to the output of NAND circuit $ND_5$. The output of OR circuit $OR_1$ is connected through resistor $R_{30}$ to the base of transistor $Q_6$. The transistor $Q_6$, which is of an NPN type, has its collector connected through the electromagnet 66 to the bus $E_{30}$, and has its emitter connected to the bus $E_4$. Resistor $R_{31}$ is connected across the base and emitter of transistor $Q_6$. It will be noted that resistors $R_{52}$, $R_{54}$, $R_{55}$ and $R_{53}$, which form, together with associated capacitors $C_{42}$, $C_{44}$, $C_{45}$ and $C_{43}$, operation stabilizing differentiators, are connected across the other input of NAND circuit $ND_3$, the one input of NAND circuit $ND_4$, the other input of NAND circuit $ND_5$ and the other input of NAND circuit $ND_6$, respectively, and the bus $E_3$.

The specific circuit of the light source unit 62 which is shown in FIG. 9 generally operates in the similar manner as the circuit shown in FIG. 5 with certain exceptions, which will be briefly described below.

When the shutter release switch 31 (see FIG. 4) is closed, an "L" level signal is fed through the synchronizing contact 25 and the sequence control circuit 71 to the other input of NAND circuit $ND_3$ in the photographing light source control circuit 76, whereby the flipflop formed by circuits $ND_3$ and $ND_4$ is set to provide a signal which is fed through OR circuit $OR_1$ to turn transistor $Q_6$ on, thus energizing the electromagnet 66. Consequently, the light shield member 65 is moved to intercept the light path, thus intercepting the light from the light 63 which is used as the diagnostic light.

When a time interval $T_3$ passes and the output of timer circuit $TM_5$ reverts to an "L" level, the flipflop formed by circuits $ND_3$ and $ND_4$ is reset, whereby transistor $Q_6$ is turned off to deenergize the electromagnet 66, thus moving the light shield member 65 out of the light path. Consequently, the light from the light 63 is supplied as photographing light.

When a proper exposure has been given to the film surface, the operational amplifier $OP_2$ in the exposure calculation circuit 73 has its output reverted to an "H" level, which is supplied as an "L" level signal through inverter $IN_4$ to be applied to the other input of NAND circuit $ND_5$. This sets the flipflop formed by NAND circuits $ND_5$ and $ND_6$, producing a signal which is fed through OR circuit $OR_1$ to turn transistor $Q_6$ on. Hence, the electromagnet 66 is energized to move the light shield member 65 onto the light path, intercepting the photographing light from the light 63.

When the preset shutter period passes, the synchronizing contact 25 is closed, whereby a trigger signal of an "L" level is applied to the fourth delay circuit 75 through inverter $IN_3$. The output of timer $TM_6$ then changes to an "H" level, but the flipflop formed by NAND circuits $ND_5$ and $ND_6$ maintains its current position in which the light shield member 65 is maintained on the light path. When the time interval $T_4$ passes subsequently, the output of timer circuit $TM_6$ reverses, resetting the flipflop formed by NAND circuits $ND_5$ and $ND_6$ to turn transistor $Q_6$ off, thus deenergizing the electromagnet 66. Consequently, the light shield member 65 is moved out of the light path, allowing the light from the light 63 to be passed as the diagnostic light.

In this manner, the electromagnet 66 is energized twice, providing a complete separation between the diagnostic and the photographing light, enabling an exposure control of a high accuracy.

In the embodiments described above, the film winding motor 24 is disposed in the camera 4 to wind up the film 22. However, it should be understood that the film winding operation may be manually performed. In this instance, it will be appreciated that there is no need to provide the fifth delay circuit 36 within the camera 4 for initiating a film winding operation by the motor 24 after the shutter 20 has been fully closed.

What is claimed is:

1. An apparatus for endoscopic photography, comprising:

a light source unit that includes light source means for introducing into the endoscope both diagnostic light, to enable the operator to examine the object that is to be examined, and photographing light, for making a photograph of the object; said light source unit further including means for interrupting the introduction of said diagnostic light into the endoscope;

first delay circuit means for initiating the opening of a shutter of a camera responsive to the depression of a shutter release button of the camera after the introduction of said diagnostic light from said light source unit into the endoscope is interrupted;

an exposure calculating circuit for determining a proper exposure;

second delay circuit means for causing said exposure calculation circuit to initiate its operation a first predetermined time after the shutter is opened;

third delay circuit means for allowing the introduction of said photographing light from said light source unit into the endoscope a second predetermined time after the initiation of operation of said exposure calculation circuit; and fourth delay circuit means for reinitiating the introduction of said diagnostic light from said light source unit into the endoscope after completion of the exposure of a film disposed within the camera and after the shutter has been fully closed.

2. An apparatus for endoscopic photography, comprising:

a light source unit that includes light source means for introducing into the endoscope both diagnostic light, to enable the operator to examine the object that is to be examined, and photographing light, for making a photograph of the object; said light source unit further including means for interrupting the introduction of said diagnostic light into the endoscope;

first delay circuit means for initiating the opening of a shutter of a camera responsive to the depression of a shutter release button of the camera after the introduction of said diagnostic light from said light source unit into the endoscope is interrupted;

an exposure calculating circuit for determining a proper exposure;

second delay circuit means for causing said exposure calculation circuit to initiate its operation a first predetermined time after the shutter is opened;

third delay circuit means for allowing the introduction of said photographing light from said light source unit into the endoscope a second predetermined time after the initiation of operation of said exposure calculation circuit;

fourth delay circuit means for reinitiating the introduction of said diagnostic light from said light source unit into the endoscope after completion of the exposure of a film disposed within the camera and after the shutter has been fully closed; and fifth delay circuit means for causing a film winding operation to be initiated in the camera after the shutter has been fully closed.

3. An apparatus according to claim 1 or 2, in which said light source unit includes a first source of diagnostic light and a second source of photographing light, and in which said light source unit includes a movable light path switching reflecting mirror for selectively introducing said diagnostic light and said photographing light into the endoscope.

4. An apparatus according to claim 1 or 2, in which said light source unit comprises a single light source which provides both said diagnostic light and said photographing light, and in which said light source unit includes a light shield member disposed in a light path extending between said light source unit and the endoscope when said light source unit is connected to the endoscope, said light shield member being selectively movable into and out of said light path to interrupt introduction of light into the endoscope for defining a separation in time between said diagnostic light and said photographing light.

5. An apparatus according to claim 1, in which each said delay circuit means comprises a respective pulse generator including a monostable multivibrator.

6. An apparatus according to claim 2, in which each said delay circuit means comprises a respective pulse generator including a monostable multivibrator.

7. An apparatus according to claim 1 or 2, in which said first delay circuit means is for initiating the opening of a mirror shutter.

8. An apparatus according to claim 1 or 2, further comprising synchronizing means for actuating said second, third and fourth delay circuit means after actuation of said first delay circuit means, said synchronizing means comprising a semiconductor switching circuit.

9. An apparatus according to claim 1 or 2, in which said light source unit includes a first source if diagnostic light and a second source of photographing light and wherein said second source of photographing light comprises a flash discharge tube that is adapted to be automatically controlled by an illumination control circuit associated with an electronic flash in the camera.

* * * * *